(12) United States Patent
Wohland (10) Patent No.: US 7,998,407 B2
(45) Date of Patent: Aug. 16, 2011

(54) MEASUREMENT SYSTEM FOR MEASURING SUBSTANCE CONCENTRATIONS IN LIQUID MEDIA

(75) Inventor: Albert Wohland, Viernheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 447 days.

(21) Appl. No.: 11/793,794

(22) PCT Filed: Dec. 20, 2005

(86) PCT No.: PCT/EP2005/013701
§ 371 (c)(1),
(2), (4) Date: Oct. 15, 2007

(87) PCT Pub. No.: WO2006/069675
PCT Pub. Date: Jul. 6, 2006

(65) Prior Publication Data
US 2008/0145277 A1    Jun. 19, 2008

(30) Foreign Application Priority Data
Dec. 23, 2004 (DE) .......................... 10 2004 062 255

(51) Int. Cl.
*G01N 21/00* (2006.01)
*G01N 33/00* (2006.01)
*G01N 33/48* (2006.01)
*G01N 27/00* (2006.01)
*G06F 13/00* (2006.01)
*A61B 5/05* (2006.01)

(52) U.S. Cl. ............. 422/58; 422/55; 422/61; 422/68.1; 422/82.01; 422/82.05; 436/46; 436/95; 600/347; 600/365; 710/33

(58) Field of Classification Search ................ 422/82.01
See application file for complete search history.

(56) References Cited

U.S. PATENT DOCUMENTS
4,419,016 A * 12/1983 Zoltan ............................ 368/10
(Continued)

FOREIGN PATENT DOCUMENTS
DE         100 59 539 A1      9/2001
(Continued)

OTHER PUBLICATIONS

Med$^{IC}$ eCAP Compliance Monitor, Introducing the Med-ic™ eCAP™ Compliance Monitor (2pp).
(Continued)

*Primary Examiner* — Jill Warden
*Assistant Examiner* — Jennifer Wecker (57) ABSTRACT

A system and method for measuring substance concentrations is provided. The system has a test strip container for receiving a test strip(s). The container has a sealing device, a counter device that counts a number of opening processes of the sealing device, a data carrier that stores batch-specific data of the test strip(s), a data transmission device for wireless transmission of the data and of the number. An analysis module has a device for measuring substance concentrations by the test strip(s), and a data-receiving device for wireless reception of the data from the data transmission device and of the number. The method records the number and stores the number on the data carrier; sends data and the number by wireless transmission to the analysis module, and determines a substance concentration by the test strip(s). Also or instead, the counter device counts a time duration of the opening processes.

21 Claims, 2 Drawing Sheets

U.S. PATENT DOCUMENTS

| | | | |
|---|---|---|---|
| 5,307,263 A | 4/1994 | Brown | |
| 5,505,308 A | 4/1996 | Eikmeier et al. | |
| 6,605,471 B1 | 8/2003 | Lundsgaard et al. | |
| 6,881,578 B2 * | 4/2005 | Otake | 436/44 |
| 7,175,081 B2 | 2/2007 | Andreasson et al. | |
| 2003/0223906 A1 * | 12/2003 | McAllister et al. | 422/58 |
| 2004/0249999 A1 * | 12/2004 | Connolly et al. | 710/33 |
| 2006/0151342 A1 | 7/2006 | Yaguchi | |
| 2007/0237678 A1 * | 10/2007 | Roesicke et al. | 422/82.01 |

FOREIGN PATENT DOCUMENTS

| | | |
|---|---|---|
| DE | 102 37 602 A1 | 3/2004 |
| EP | 1 225 448 A2 | 7/2002 |
| GB | 2 210 56 A | 9/1924 |
| JP | 1984-025749 A | 2/1984 |
| JP | 1984-189743 A | 10/1984 |
| JP | 1986-105686 U | 7/1986 |
| JP | 1995-069360 A | 3/1995 |
| JP | 1999-514087 A | 11/1999 |
| JP | 2001-281199 A | 10/2001 |
| JP | 2002-196003 A | 7/2002 |
| JP | 2004-139345 A | 5/2004 |
| JP | 2004/068128 A1 | 8/2004 |
| JP | 2004-354300 A | 12/2004 |
| JP | 2008-502901 A | 1/2008 |
| WO | WO 94/27117 | 11/1994 |
| WO | WO 02/078533 A2 | 10/2002 |
| WO | WO 03/082091 A2 | 10/2003 |
| WO | WO 03/091678 A1 | 11/2003 |
| WO | WO 2004/090503 A | 10/2004 |
| WO | 2006/009534 A1 | 1/2006 |

OTHER PUBLICATIONS 1984-189743 A Patent Abstract of Japan.
2001-281199 A Patent Abstract of Japan.
2002-196003 A Patent Abstract of Japan.
2004-139345 A Patent Abstract of Japan.
2004-354300 A Patent Abstract of Japan.
Japan Patent Application No. 2007-547317, Office Action (translation-in-part) dated Apr. 27, 2010.

* cited by examiner

MEASUREMENT SYSTEM FOR MEASURING SUBSTANCE CONCENTRATIONS IN LIQUID MEDIA

REFERENCE TO RELATED APPLICATIONS

This application claims priority to PCT/EP2005/013701, filed Dec. 20, 2005 and DE 10 2004 062 255.8, filed on Dec. 23, 2004.

TECHNICAL FIELD

The invention concerns a portable analytical measurement system for measuring substance concentrations in liquid media.

BACKGROUND

The monitoring of blood glucose concentrations is an essential part of the daily routine of diabetics. The blood glucose concentration has to be determined quickly and simply several times a day in order, if appropriate, to be able to take suitable medical measures. So as not to restrict the diabetic's daily routine any more than is necessary, suitable portable devices are often employed which are intended to be easy to carry around and to operate, such that the blood glucose concentration can be measured, for example, at the workplace or even during leisure time.

Various portable devices are presently available on the market, some of them functioning according to different measurement methods. Various diagnostic methods are used in these devices, for example optical or even electrochemical measurement methods. One example of a frequently used measurement method makes use of a special kind of electrochemical test strip. These test strips are, for example, configured in such a way that a predetermined quantity of blood is conveyed to an electrode system via a capillary system in the test strip. For modem test strips, a quantity of blood of ca. 1.5 µl is sufficient; sometimes even quantities of blood of less than 1 µl. The electrode system may, for example, involve gold electrodes that are provided with a coating. The coating contains at least different enzymes and so-called mediators and has the effect that charge carriers (for example in the form of redox molecules) form within the sample on the electrodes, the concentration of these charge carriers being dependent on the blood glucose concentration. The concentration of these charge carriers can be determined by means of the gold electrodes and a suitable measurement system, for example by means of a current-voltage measurement, and from this concentration it is possible, finally, to calculate the blood glucose concentration.

An important element of these diagnostic systems is therefore represented by the corresponding test strips. Typically, about 5 to 7 such test strips are needed each day by a diabetic. It is essential that the test strips are kept clean and dry, in order to ensure that the measurement of the blood glucose concentration is not rendered inaccurate by their contamination or by the action of moisture.

However, a problem that often arises is that the user or patient does not correctly close a test strip container for test strips after he or she has removed one or more test strips. It can also happen that the test strip container is not closed at all for quite a long time. The resulting lack of a tight seal and the effect of air on the test strips can lead to a deterioration in the quality of the test strips and to false measurement results.

A further problem with the test strips is that the properties of the test strips used may often vary from batch to batch. This leads to in some cases huge variations in the accuracy of the blood glucose concentration measurement. In many known commercial systems, batch information relating to the test strips therefore has to be input into an analysis module prior to a corresponding blood glucose concentration measurement, so that the analysis module can correctly "interpret" the measurement data of the test strip by means of this batch information, in order to determine a correct blood glucose concentration from said data. There are several known methods for inputting the batch information into the analysis module. For example, it is possible here to use suitable barcodes which, for example, are arranged on the test strip container and can be read out by the analysis module. Alternatively, systems are also known in which a data carrier, often also called a ROM key, is attached to the test strip container holding the test strips. This data carrier can, for example, be attached loosely to the closed test strip container for the test strips, or it can also be integrated fixedly into the test strip container. However, if this ROM key is lost (for example by its coming loose from the test strip container), then the batch information is also lost along with it, and the test strips are therefore by and large unusable.

Moreover, the known ways of transmitting batch information into the analysis module have the disadvantage that they presuppose a corresponding action on the part of the user or patient. Automatic transmission of batch information does not take place. However, if the user or patient forgets to transmit this batch information, or if an error occurs when transmitting the batch information, this can have the consequence, for example, of the blood glucose concentrations being calculated incorrectly. This may cause incorrect medical counter-measures to be taken, for example in the form of incorrect dosages of insulin, which can have adverse consequences for the patient.

EP 0 101 812 B1, also published as U.S. Pat. No. 4,419,016 discloses a device for presentation of medicaments, in which a medicament is dispensed from a container that comprises a cap, and a sensor device records when the cap of the container is opened. The container also comprises a clock which records the times at which the cap is opened or closed. A device and display are also provided which notify a patient when a medicament has to be taken again.

From the field of pharmacy, several systems are known in which pharmaceutical products are traced by means of what are known as radio frequency identification (RFID) tags. Such a system is known from WO 03/071943, also published as U.S. Pat. No. 7,175,081 B2, for example. In the arrangement described in the latter, medicinal products are provided with RFID tags and stored in a suitable storage cabinet. A receiver device, which is coupled to a corresponding processor, receives the signals from the RFID tags of the medicinal products and can, for example, automatically organize the management of these products.

SUMMARY OF THE INVENTION

The invention relates to a portable analytical measurement system for measuring substance concentrations in liquid media, in particular to a measurement system for measuring blood glucose concentrations and/or blood fat concentrations. The invention further relates to a method for measuring substance concentrations in liquid media by means of a measurement system according to the invention, and to the use of an "intelligent" test strip container in a measurement system of this kind for measuring substance concentrations in liquid media.

The present invention makes available a system that permits simple and reliable measurement of substance concentrations in liquid media by means of test strips. The described system is in particular intended to avoid the aforementioned disadvantages of the prior art, to ensure that the test strips are kept dry and clean, and to allow correct batch information concerning the test strips to be used at all times.

A portable analytical measurement system for measuring substance concentrations in a liquid media is provided. The system comprises a test strip container for receiving at least one test strip. The test strip container includes a sealing device, a counter device for counting a number of opening processes of the sealing device, a data carrier for storage of batch-specific data of the at least one test strip, and a data transmission device for wireless transmission of the batch-specific data and of the number of opening processes of the sealing device. The system further comprises an analysis module. The analysis module includes a device for measuring substance concentrations in the liquid media by the at least one test strip, and a data-receiving device for wireless reception of the batch-specific data from the data transmission device and of the number of opening processes of the sealing device.

A portable analytical measurement system for measuring substance concentrations in liquid media is further provided. The system comprises a test strip container for receiving at least one test strip. The test strip container includes a sealing device, a counter device for counting a time duration of opening processes of the sealing device, a data carrier for storage of batch-specific data of the test strips and a time duration of opening processes, and a data transmission device for wireless transmission of the time duration of opening processes to an analysis module. The system further includes an analysis module having a device for measuring substance concentrations in liquid media by the at least one test strip, and a data-receiving device for wireless reception of batch-specific data from the data transmission device and of the time duration of opening processes.

A method for measuring substance concentrations in liquid media is provided. The method comprises the steps of providing a measurement system having a test strip container for receiving at least one test strip, said test strip container including a sealing device, a counter device for counting a number of opening processes of the sealing device, a data carrier for storage of batch-specific data of the test strips, a data transmission device for wireless transmission of batch-specific data and of the number of opening processes of the sealing device and an analysis module, said analysis module including a device for measuring substance concentrations in liquid media using the at least one test strip, and a data-receiving device for wireless reception of batch specific data from the data transmission device and of a number of opening processes, recording a number of opening processes by the counter device and storing the number on the data carrier; sending batch-specific data and a number of opening processes by wireless transmission to the analysis module, and determining a substance concentration in the liquid medium by the at least one test strip.

A portable analytical measurement system for measuring substance concentrations in liquid media is provided. This can, for example, involve measuring blood glucose concentrations and/or blood fat concentrations. However, in an alternative to this, or in addition, other substance concentrations can also be determined, or corresponding other analyses can be carried out, for example pH measurements or similar analyses. Liquid media are to be understood in particular here as liquid samples or gaseous samples.

The measurement system comprises a test strip container for receiving at least one test strip. These test strips can, for example, be one of the abovementioned test strips for an electrochemical and/or photometric analysis of liquid samples. They can in particular be test strips of the above-described type with a capillary system and one or more electrodes and with additional chemical auxiliaries (for example enzymes and mediators). "Test strips" are to be understood, by analogy, as also meaning other test vehicles, in particular small test tubes or even continuous rolls of test strips.

The test strip container comprises at least one sealing device for closing the test strip container or for opening the test strip container for the purpose of removing one or more test strips. This sealing device can be configured in different ways. In particular, this sealing device can be designed such that the test strip container is able to be sealed hermetically by means of the sealing device. In this way, test strips held in the test strip container are protected against the effects of air moisture or atmospheric oxygen and other contaminants. The sealing device can, for example, be designed such that it comprises a simple stopper which is pressed into an opening of the test strip container in order to seal the latter. This stopper can in particular be loose, or it can also be connected to the test strip container via a flexible connection piece, thus reducing the chance of the stopper being lost while the test strip container is in the opened state. Alternatively, or in addition to this, the sealing device can, for example, also comprise a lid with a hinge, in which case the lid ideally seals the test strip container hermetically in the closed state.

The test strip container also comprises a counter device for counting a number and/or a time duration of opening processes of the sealing device, and a data carrier for storage of batch-specific data of the test strips and/or of a number and/or time duration of opening processes. The counter device can, for example, comprise a clock and a corresponding element (for example an element as described in EP 0 101 812 B1, also published as U.S. Pat. No. 4,419,016) which records the opening of the sealing device and, for example, increases a timer by one step upon each opening. As soon as an opening of the sealing device is recorded, the element can also start a time counter, for example a clock, which then stops again when the sealing device is subsequently closed. In this way, the times during which the test strip container is opened can be determined. In particular, individual times can be recorded in this way, or times can also be recorded cumulatively. The times thus recorded, or the recorded number of opening processes of the sealing device, can be stored in particular on the data carrier. Moreover, as has been described above, batch-specific data of the test strips can be stored on the data carrier.

The test strip container moreover comprises a data transmission device for wireless transmission of batch-specific data and a number and/or time duration of opening processes to an analysis module. In particular, the data stored on the data carrier can be transmitted by means of this data transmission device. The data transmission to the analysis module is intended to involve wireless transmission. In particular, the data transmission device can comprise at least one transponder. A transponder can in this case be understood in particular as a radiofrequency identification (RFID) tag or as a device comprising such an RFID tag. In particular, the transponder can also comprise a microprocessor and also have its own memory. Moreover, the transponder has at least one antenna for transmitting data, for example a copper coil printed onto a substrate. Moreover, the transponder can have its own energy source, for example a battery. Alternatively, or in addition to this, the transponder can also be supplied with energy from an external source, for example by receiving suitable electromagnetic waves, which are emitted, for example, from an analysis module. The transponder can be designed to only send data, but may also be designed both to send data and also to receive data. In particular, the transponder can send data in a frequency range of ca. 900 MHz.

The measurement system further comprises an analysis module with a device for measuring substance concentrations in liquid media by means of a test strip. This can, for example, be an analysis module that basically has the functions known from the prior art for a measurement appliance that measures blood glucose concentrations. In particular, it can be an analysis module which, determines blood glucose concentrations by means of an electrochemical or optical measurement method, each of which are well known in the prior art. Analysis modules of this kind are known from the prior art, and the other functions of these modules do not therefore need to be described in any more detail here.

The analysis module according to the invention further comprises a data-receiving device for wireless reception of batch-specific data and of a number and/or time duration of opening processes. This data-receiving device can be used to receive, for example, the information (see above) emitted by the data-transmitting device in the test strip container. The data-receiving device can be designed purely as a receiving device, although it may also involve a device that has both a receiving device and also a transmitting device. Thus, the data-receiving device can, for example, have a transmitting device which initially sends a wireless signal (for example emitted at regular intervals) to a data-transmitting device in a test strip container which is possibly situated in proximity to the analysis module, and prompts it for wireless transmission of data. These data are then received by the analysis module by way of the data-receiving device. Moreover, as has been described above, the data-receiving device can, for example, also be used at the same time to supply energy to the data-transmitting device in a test strip container via electromagnetic waves. The electromagnetic waves for exchange of data and energy between the analysis module and the test strip container can be understood, for example, as radiofrequency waves, or as electromagnetic waves in the infrared spectral range. Other spectral ranges of the electromagnetic spectrum are also conceivable.

The measurement system can in particular be designed such that the analysis module has a warning device for warning a user. If, for example, it is established, on the basis of the transmission of data from the test strip container, that the test strip container has been opened too often, i.e. more often that a predetermined number, a warning can be output to a person using the measurement system. This warning can, for example, be in the form of an acoustic signal or in the form of an optical indication, for example an indication provided by an LCD or an indication on a display screen. It is also possible, again for example on the basis of the data transmitted from the test strip container, to determine whether the test strip container was opened for too long. This can involve a maximum overall time duration of opening processes of the test strip container, or also the duration of a single opening process. This avoids a situation where the user measures substance concentrations using test strips that have been exposed for too long to the atmosphere and to air moisture. Alternatively, or in addition to this, other warning functions can be provided. For example, assuming that a test strip is removed from the test strip container each time the latter is opened, it is possible, from the maximum number of opening processes, to conclude that only a certain number of test strips are still left in the test strip container. For example, the person using the measurement system can be informed of this number of remaining test strips via an indicator device, for example a display in the analysis module. A warning can also be given if the test strip container is empty. Other warning signs too can be generated. For example, if the test strip container includes a moisture sensor that measures the overall exposure of the test strips to air moisture in the test strip container, this information is transmitted to the analysis module by the data-transmitting device, and this information is then evaluated to ascertain whether the test strips have been exposed for too long to a defined maximum quantity of air moisture.

The measurement of substance concentrations in liquid media by means of the test strips can then take place in the analysis module, in particular with the aid of the data transmitted from the test strip container. Thus, in particular, the batch information, or the batch-specific data, can be used to calculate the substance concentrations. For this purpose, the analysis module can comprise a suitable evaluation device. Other data too, for example data on the moisture taken up in the test strips, can be entered into the calculation of the substance concentrations. For example, a calibration can be performed which takes account of how the calculation of the substance concentration is to be modified if a test strip has taken up a defined quantity of air moisture. This information can be stored in the analysis module, for example in the evaluation device, for example in an electronic table (e.g. a lookup table).

In addition, a method for measuring substance concentrations in liquid media using a measurement system according to the invention (as described above) is provided.

The described measurement system and the corresponding method for use of the measurement system have numerous advantages over conventional systems and methods. An important advantage lies in the fact that batch-specific data of the test strips, in particular calibration data and possibly further information, are transmitted automatically from the test strip container to the analysis module. An intervention on the part of the user, for example in the form of reading out a ROM key or a barcode, is not necessary. This considerably increases the safety of handling of the measurement system, since errors associated with entering batch-specific information into the analysis module are greatly reduced or made unlikely. Moreover, there is no longer a danger of data carriers, in particular ROM keys, loosely mounted on the test strip container being lost during handling of the test strip container. The data carrier in the test strip container cannot be lost, because it is a component part of the test strip container, for example being integrated into the sealing device, which is in turn required for closing the test strip container.

The reliability of the measurement of substance concentrations is also greatly improved by the knowledge of the condition of the test strips. The information on how often and for how long the test strip container was opened, and accordingly how often the test strips were exposed to the air and to air moisture, prevents or greatly reduces measurement discrepancies or and also incorrect measurements which, as has been described above, could lead to adverse consequences for the user or patient.

BRIEF DESCRIPTION OF THE DRAWINGS

The invention is described in more detail below on the basis of illustrative embodiments. However, the invention is not limited to the illustrative embodiments shown. The illustrative embodiments are shown schematically in the figures. Identical reference numbers in the individual figures designate identical elements or designate elements which are of identical function or which correspond to one another in terms of their function.

DETAILED DESCRIPTION OF THE DRAWINGS

Figure 1:
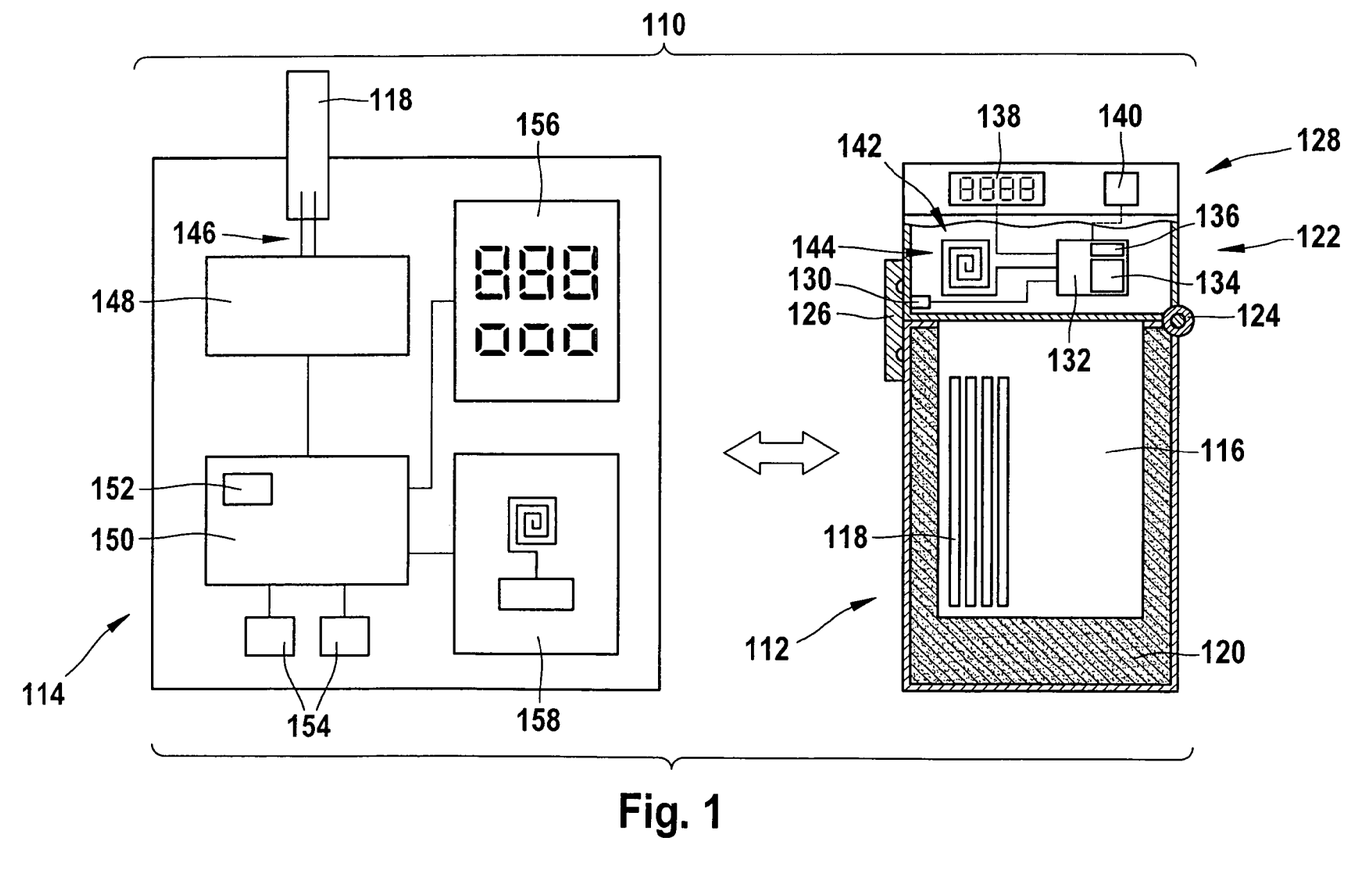
FIG. 1 shows an illustrative embodiment of a portable analytical measurement system for measuring substance concentrations in liquid media, with a test strip container and an analysis module.

FIG. 1 shows a portable analytical measurement system 110 for measuring substance concentrations in liquid media, in particular for measuring blood glucose concentrations. The measurement system 110 comprises a test strip container 112 and an analysis module 114. The test strip container 112 comprises a storage space 116 in which a number of test strips 118 are stored. In this illustrative embodiment, the test strips 118 are test strips 118 that correspond to the prior art and that are used for measuring blood glucose concentrations by means of an electrochemical measurement method.

The test strips 118 are sensitive to moisture. For this reason, the storage space 116 contains a desiccant 120, which reduces the air moisture in the interior of the storage space 116. The storage space 116 also has a sealing device 122. The sealing device 122 comprises a hinge 124, a closure element 126 and a lid 128. By means of the sealing device 122, the storage space 116 can be sealed in an airtight manner, by the lid 128 being closed via the hinge 124 and fixed via the closure element 126. The edge of the lid 128 can additionally be provided with an O-ring in order to provide additional sealing of the storage space 116.

In this illustrative embodiment, the lid 128 is designed as a so-called electronic lid (eCap) 128, similar to the device described in EP 0 101 812 B1, also published as U.S. Pat. No. 4,419,016. For this purpose, the lid 128 has an opening sensor 130 which records whether the sealing device 122 is opened or closed. This opening sensor 130 can be designed in different ways and can, for example, comprise one or more electrical contacts and a resilient member, such that, upon closure of the sealing device 122 by means of the resilient member, an electrical connection is established between the contacts. An opening sensor of this kind is described in EP 0 101 812 B1, also published as U.S. Pat. No. 4,419,016, for example, and therefore does not need be described in any more detail here.

The opening sensor 130 is connected to a microprocessor 132 which comprises a counter device 134 (for example in the form of an electronic timer, in particular a clock). The microprocessor 132 also comprises a data carrier 136, for example in the form of a volatile memory random access memory (RAM) or a read-only memory, in particular an Erasable Programmable ROM (EPROM). The microprocessor 132 can also have several data carriers 136, for example a volatile memory for continuous storage and reading-out of information concerning the opening processes of the sealing device 122, and a read-only memory in the form of an EPROM for storage and reading-out of batch-specific information concerning the test strips 118.

The microprocessor 132 is also connected to a display element 138 in the form of a simple liquid crystal display (LCD) and to an operating element 140, for example in the form of one or more push-buttons. Finally, the microprocessor 132 is connected to a transmitting and receiving device 142, which is indicated symbolically in FIG. 1 as a loop antenna. Other antenna forms are also possible. In addition to the loop antenna, however, the transmitting and receiving device 142 can also comprise a number of other elements (not shown), for example corresponding other components of an electrical oscillating circuit, such as capacitors and resistors. This transmitting and receiving device 142 can in particular also be designed as a printed circuit. The microprocessor 132 and the transmitting and receiving device 142 together form a transponder 144 in this illustrative embodiment.

As has been described above, the portable analytical measurement system 110 also comprises an analysis module 114. The analysis module 114 is designed in particular to receive a test strip 118, this test strip 118 being electrically contacted by means of a measurement electrode system 146. As has been described above, charge concentrations can be determined using a suitable evaluation device 148, for example an electronic circuit for impedance measurement or current-voltage measurement, and the blood glucose concentration of a droplet of blood applied to the test strip 118 can then be calculated from this. Such devices are known from the prior art and are already commercially available at present in the form of corresponding measurement appliances.

The evaluation device 148 is also connected to a microprocessor 150. The microprocessor 150 comprises one or more data memories 152, for example once again in the form of volatile memories or also in the form of non-volatile memories. The microprocessor 150 is also connected to operating elements 154, for example in the form of push-buttons, which are arranged on a user interface of the analysis module 114 and via which a user can operate the analysis module 114. The analysis module 114 is also provided with a display element 156 which is connected to the microprocessor 150. From this display element 156, which can once again comprise an LCD for example, a user is able to read off the results of the measurement of the blood glucose concentration, for example.

Moreover, the analysis module 114 again comprises a transmitting and receiving device 158, which is connected to the microprocessor 150. In this illustrative embodiment, the transmitting and receiving device 158 is again indicated symbolically by a loop antenna, but, as in the case of the test strip container 112 too, it can again comprise a number of additional electronic components (not shown), in particular a number of capacitors, resistors, or active electronic components and its own microprocessors.

The described measurement system 110 has a number of functions adapted to the particular requirements of monitoring of blood glucose concentration by a patient. Thus, in addition to the function of permitting dry and clean storage of the test strips 118 in the storage space 116, the test strip container 112 in particular has a number of warning functions and information functions. Thus, the microprocessor 132 records each opening and closing of the sealing device 122 detected by means of the opening sensor 130. In particular, the microprocessor 132 can generate an acoustic warning signal (via a loudspeaker not shown here) or an optical warning signal (for example via a light-emitting diode or the display element 138) when the opening sensor 130 detects that the sealing device 122 has not been closed for quite a long time. In this way, a person using the test strip container 112 can immediately step in and close the test strip container 112 accordingly.

Moreover, the number of times the sealing device 122 is opened and closed can be recorded by the counter device 134. This information can be made use of for various purposes. On the one hand, assuming that a test strip 118 is removed from the storage space 116 upon each opening process, the "filling level" of the test strip container 112 can be monitored and transmitted to the user. For example, the number of test strips 118 can be counted back from an original number, such that a person using the test strip container 112 is promptly alerted when the test strips 118 in the test strip container 112 begin to run out. In particular, the user can, for example, arrange to be warned when a defined minimum number of test strips 118 are present in the test strip container 112, so as to be able to refill the test strip container 112 in good time.

Moreover, the quantity of air moisture in the storage space 116 can be calculated from the number of times the sealing device 122 has been opened and closed and from the overall duration of the opening procedures. For example, the time intervals during which the test strip container 112 was opened, which intervals are determined by means of the counter device 134, can be added by the microprocessor 132 to an overall opening duration. If a defined maximum overall duration is exceeded, a warning signal can, for example, be output to a user. In addition, or as an alternative to this, the microprocessor 132 can also be connected to a moisture sensor (not shown) which is located in the storage space 116 of the test strip container 112 and which permanently monitors the air moisture in the storage space 116 and transmits to the microprocessor.

The microprocessor 132 can be programmed by the user via the operating element 140, and information can be conveyed to the user in the opposite direction via the display element 138. Thus, for example, the user can also indicate that he would like the microprocessor 132 to remind him at regular intervals, which can be defined by the user, that a blood glucose concentration measurement has to be performed (this reminder again being given as an optical or acoustic signal).

Instead of a direct communication of the microprocessor 132 with the user via optical or acoustic signals, all the functions can, for example, also be taken over by the analysis module 114. For this purpose, all the information available to the microprocessor 132 of the test strip container 112 can be transmitted to the analysis module 114 via the transmitting and receiving device 142. This can be done in particular by the transmitting and receiving device 158 in the analysis module 114 emitting, at regular intervals, signals that can be received by a transponder 144 of a test strip container 112 located in the vicinity. For its part, the transponder 144 of the test strip container 112 can in turn send a corresponding signal back to the analysis module 114. In this way, the measurement system 110 identifies that a test strip container 112 and an analysis module 114 are in sufficient spatial proximity to one another and are able to exchange data. A corresponding exchange of data between the microprocessor 132 of the test strip container 112 and the microprocessor 150 of the analysis module 114 can then take place. Thus, for example, the analysis module 114 can request information from the test strip container 112, for example information on whether there are still test strips 118 in the storage space 116 of the test strip container 112 and, if appropriate, what state (regarding uptake of air moisture or the like) the test strips 118 are in. Corresponding information can then be sent from the microprocessor 150 of the analysis module 114 to the user, for example via the display element 156 of the analysis module 114 or via suitable acoustic signals. Thus, for example, the analysis module 114 can also notify a user that new test strips 118 need to be introduced into the storage space 116 of the test strip container 112, or that the time for renewed determination of the blood glucose concentration has arrived. Since the analysis module 114 usually has a more powerful microprocessor 150 with more comprehensive operating elements 154, the microprocessor 132 in the test strip container 112 can also be programmed on the analysis module 114. This has the advantage of increased user-friendliness and of extending the range of functions of the measurement system 110.

Moreover, batch information can also be transmitted automatically between the test strip container 112 and the analysis module 114. For this purpose, corresponding batch-specific information concerning the test strips 118 in the test strip container 112 can be stored in the data carrier 136 of the microprocessor 132, for example in an EPROM. This can be done in various ways. For example, the test strip container 112 can be designed as a disposable container, and a user obtains the full test strip container 112 from a drugstore, for example. In such a case, batch-specific information concerning the test strips 118 is already stored in the data carrier 136 of the electronic lid 128 at the time of purchase of the test strip container 112. A suitable deposit system could also be envisioned. For example, an empty test strip container 112 returned, for example to a location, non-limiting examples of which include a drugstore or pharmaceutical wholesaler, can then be refilled with test strips 118, in which case either the transponder 144 or component parts thereof is completely replaced, or, alternatively, new batch-specific information concerning the test strips 118 can also be introduced into the microprocessor 132 via the transmitting and receiving device 142. Alternatively, when obtaining test strips 118, a user can also obtain a corresponding transponder 144 or component parts thereof, together with instructions on fitting this transponder 144 into the lid 122 of the test strip container 112.

The transmission of batch-specific information from the data carrier 136 of the microprocessor 132 to the analysis module 114 via the transmitting and receiving device 142 can take place automatically with the measurement system 110 shown. For example, as soon as it has been established (see above) that a suitable test strip container 112 is located at a proximity suitable for data transmission, the analysis module 114 can, by means of a special request signal, request that the test strip container 112 provide corresponding batch-specific information concerning the test strips 118.

FIG. 1 does not show the energy supplies of the analysis module 114 and of the test strip container 112. The analysis module 114 can be supplied with electrical energy via a set of batteries, for example. The means of supplying electrical energy to the test strip container 112 is more complex, because there is only a small amount of space available, particularly in the lid 128, for a corresponding arrangement of batteries. However, a suitable electrical button cell can be inserted, for energy supply, into the lid 128, for example. Alternatively, or in addition to this, it is also possible to use an energy supply system in which the lid 128 is supplied with energy by electromagnetic waves, for example, which are transmitted from the analysis module 114, specifically from the transmitting and receiving device 158, to the test strip container 112. These electromagnetic waves can be received, for example, in particular by the transmitting and receiving device 142 of the lid 128 and can be used, for example, to charge a corresponding energy source, for example a capacitor. A principle of this kind is already used at present in various transponder devices in other technical fields. A separation of the functions in the lid 128 is also conceivable, for example a separate energy supply for the transmitting and receiving device 142 and the microprocessor 132. Thus, for example, the request for data by the analysis module 114 can be generated by a corresponding signal which is emitted from the transmitting and receiving device 158 of the analysis module 114, and these electromagnetic waves are received by the transmitting and receiving device 142 of the test strip container 112, where a corresponding energy source is charged, so as to be able then to send the requested data back to the analysis module 114.

Figure 2:
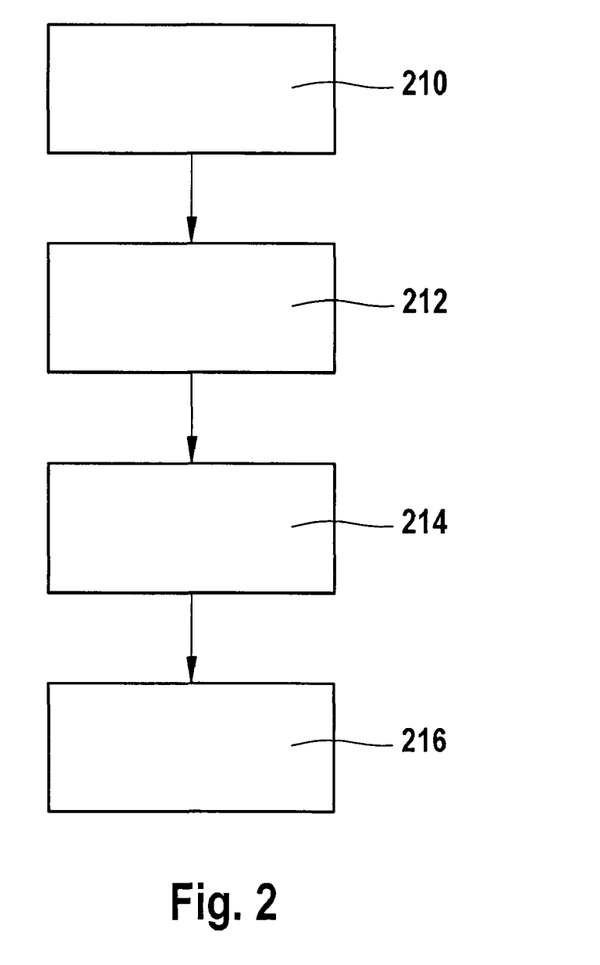
FIG. 2 shows a flow chart of a method for measuring substance concentrations in liquid media by means of a measurement system according to the invention.

FIG. 2 shows a method for measuring substance concentrations in liquid media by means of a measurement system 110, for example the measurement system 110 described in FIG. 1. The steps shown do not necessarily have to be carried out in the sequence illustrated here, and additional steps not shown in FIG. 2 can also be carried out.

First, in method step 210, a number and/or time duration of opening processes of a sealing device 122 is recorded by means of a counter device 134 and stored on a data carrier 136. Then, in method step 212, batch-specific data and a number and/or time duration of opening processes are sent to the analysis module 114. If, by comparing these data, the analysis module 114 determines that a maximum number of opening processes (which can be stored for example in a data memory 152 of the microprocessor 150 in the analysis module 114 and can be set by a user, for example via the operating elements 154) has been exceeded, or that a maximum overall time duration of opening processes of the test strip container 112 has been exceeded, then a corresponding warning is sent to a user of the analysis module 114 in the optional method step 214, for example in the form of an optical indication on the display 156 or in the form of an acoustic indication. Thereafter, in method step 216, a substance concentration in a liquid medium, in particular a blood glucose concentration is determined by means of a test strip 118 on the analysis module 114.

REFERENCE NUMBERS 110 portable analytical measurement system
112 test strip container
114 analysis module
116 storage space
118 test strip
120 desiccant
122 sealing device
124 hinge
126 closure element
128 lid
130 opening sensor
132 microprocessor
134 counter device
136 data carrier
138 display element
140 transmitting and receiving device
144 transponder
146 measurement electrode system
148 evaluation device
150 microprocessor
152 data memory
154 operating element
156 display element
158 transmitting and receiving device
210 recording and storage of a number of opening processes
212 transmission of data to analysis module 114
214 warning to user
216 blood glucose concentration measurement

What is claimed is:

1. A portable analytical measurement system for measuring substance concentrations in a liquid media, the system comprising:
   a) a test strip container for receiving at least one test strip, said test strip container including
      a sealing device,
      a counter device for counting a number of opening processes of the sealing device,
      a data carrier for storage of batch-specific data of the at least one test strip,
      a data transmission device for wireless transmission of the batch-specific data and of the number of opening processes of the sealing device, and
   b) an analysis module, said analysis module including
      a device for measuring substance concentrations in the liquid media by the at least one test strip, and
      a data-receiving device for wireless reception of the batch-specific data from the data transmission device and of the number of opening processes of the sealing device.

2. The measurement system of claim 1 wherein the data transmission device has at least one transponder.

3. The measurement system of claim 1 wherein the analysis module has a warning device formed to warn a user when a maximum number of opening processes has been exceeded.

4. The measurement system of claim 1 wherein the substance measurement device has an evaluation device for calculating the substance concentration as a function of the batch-specific data of the at least one test strip.

5. The measurement system of claim 1 wherein the test strip container in a closed state, is sealed off hermetically by the sealing device.

6. The measurement system of claim 1 wherein the substance measurement device has a device for measuring blood glucose concentrations.

7. The measurement system of claim 6 wherein the substance measurement device has a device for measuring blood fat concentrations.

8. The measurement system of claim 1 wherein the substance measurement device has a device for measuring blood fat concentrations.

9. The measurement system of claim 1 wherein the counter device is formed for counting a time duration of opening processes of the sealing device.

10. The measurement system of claim 1 wherein the data carrier is formed for storage of a number of opening processes of the sealing device.

11. The measurement system of claim 1 wherein the data carrier is formed for storage of a time duration of opening processes of the sealing device.

12. The measurement system of claim 1 wherein the data transmission device is formed for wireless transmission of the time duration of opening processes to the analysis module.

13. The measurement system of claim 1 wherein the data-receiving device is formed for the wireless reception of a time duration of opening processes.

14. The measurement system of claim 1 wherein the device for measuring blood glucose concentrations is an electrochemical measurement device.

15. The measurement system of claim 1 wherein the device for measuring blood glucose concentrations is an optical measurement device.

16. A portable analytical measurement system for measuring substance concentrations in liquid media, the system comprising:
   a) a test strip container for receiving at least one test strip, said test strip container including
      a sealing device,
      a counter device for counting a time duration of opening processes of the sealing device,
      a data carrier for storage of batch-specific data of the test strips and a time duration of opening processes, a data transmission device for wireless transmission of the time duration of opening processes to an analysis module, and b) an analysis module, said analysis module comprising a device for measuring substance concentrations in liquid media by the at least one test strip, and a data-receiving device for wireless reception of batch-specific data from the data transmission device and of the time duration of opening processes.

17. The measurement system of claim 16 wherein the analysis module has a warning device formed to warn a user when a maximum overall time duration of opening processes of the test strip container has been exceeded.

18. A method for measuring substance concentrations in liquid media, the method comprising the steps of:

providing a measurement system having a test strip container for receiving at least one test strip, said test strip container including a sealing device, a counter device for counting a number of opening processes of the sealing device, a data carrier for storage of batch-specific data of the test strips, a data transmission device for wireless transmission of batch-specific data and of the number of opening processes of the sealing device and an analysis module, said analysis module including a device for measuring substance concentrations in liquid media using the at least one test strip, and a data-receiving device for wireless reception of batch specific data from the data transmission device and of a number of opening processes, recording a number of opening processes by the counter device and storing the number on the data carrier;

sending batch-specific data and a number of opening processes by wireless transmission to the analysis module, and determining a substance concentration in the liquid medium by the at least one test strip.

19. The method of claim 18 further comprising the step of outputting a warning with the analysis module to a user when a maximum number of opening processes has been exceeded.

20. The method of claim 18 further comprising the steps of recording a time duration of opening processes by the counter device and storing the time on the data carrier.

21. The method of claim 20 further comprising the step of outputting a warning with the analysis module to a user when a maximum overall time duration of opening processes of the test strip container has been exceeded.

* * * * *